United States Patent
Tomita et al.

(10) Patent No.: US 7,358,492 B2
(45) Date of Patent: Apr. 15, 2008

(54) APPARATUS, METHOD, AND COMPUTER PROGRAM PRODUCT FOR DECONVOLUTION ANALYSIS

(75) Inventors: Mitsuhiro Tomita, Tokyo (JP); Hiroki Tanaka, Kanagawa (JP); Masahiko Yoshiki, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 275 days.

(21) Appl. No.: 11/330,262

(22) Filed: Jan. 12, 2006

(65) Prior Publication Data

US 2006/0278823 A1  Dec. 14, 2006

(30) Foreign Application Priority Data

Jun. 9, 2005  (JP) .............................. 2005-170148

(51) Int. Cl.
*H01J 37/252* (2006.01)
*H01J 49/14* (2006.01)
*G01N 23/225* (2006.01)
*G01N 23/227* (2006.01)

(52) U.S. Cl. .................... 250/309; 250/307; 250/305; 250/281; 250/282; 250/288

(58) Field of Classification Search ................. 250/305, 250/306, 307, 309
See application file for complete search history.

(56) References Cited

U.S. PATENT DOCUMENTS 4,510,387 A * 4/1985 Izumi et al. ................ 250/309
5,028,778 A * 7/1991 Ninomiya et al. .......... 250/305
5,637,870 A * 6/1997 Tanigaki .................... 250/307
2003/0008404 A1   1/2003 Tomita et al.

OTHER PUBLICATIONS

Shao, et al., "Response function during oxygen sputter profiling and its application to deconvolution of ultrashallow B depth profiles in Si", Applied Physics Letters, vol. 83, No. 26, pp. 5467-5469, (Dec. 29, 2003).

McConville, et al., "Determination of the erosion rate in the transient region of an ultralow energy secondary ion mass spectrometry profile using medium energy ion scattering", Journal of Vacuum Science & Technology B, vol. 20, No. 4, pp. 1690-1698, (Jul./Aug. 2002).

Tomita, et al., "Ultra-shallow depth profiling with secondary ion mass spectrometry", Journal of Vacuum Science & Technology B, vol. 22, No. 1, pp. 317-322, (Feb. 3, 2004).

Chu et al., "Dopant spatial distributions: Sample-independent response function and maximum-entropy reconstruction," Physical Review B (Dec. 15, 1997), 56: 15 167-15 170.

(Continued)

*Primary Examiner*—Jack I. Berman
(74) *Attorney, Agent, or Firm*—Finnegan, Henderson, Farabow, Garrett & Dunner, L.L.P.

(57) ABSTRACT

A deconvolution analysis apparatus includes a sputtering rate calibrating unit that calibrates a depth profile resulting from a depth analysis on a sample to be estimated by using a sputtering surface analysis, according to a depth change of a sputtering rate in an initial sputtering; and a deconvolution analysis unit that performs a deconvolution analysis on the depth profile whose depth axis is extended, so as to make a depth change of a depth resolution in the initial sputtering apparently constant.

12 Claims, 8 Drawing Sheets

OTHER PUBLICATIONS

Dowsett et al., "Secondary ion mass spectrometry analysis of ultrathin impurity layers in semiconductors and their use in quantification, instrumental assessment, and fundamental measurements," J. Vac Sci. Technol. B (Jan./Feb. 1994), 12:186-198.

* cited by examiner

APPARATUS, METHOD, AND COMPUTER PROGRAM PRODUCT FOR DECONVOLUTION ANALYSIS

CROSS-REFERENCE TO RELATED APPLICATIONS

This application is based upon and claims the benefit of priority from the prior Japanese Patent Application No. 2005-170148, filed on Jun. 9, 2005; the entire contents of which are incorporated herein by reference.

BACKGROUND OF THE INVENTION

1. Field of the Invention

The invention relates to an apparatus, a method, and a computer program product for deconvolution analysis used for calculation of true depth profile from depth profile resulting from a depth analysis by using the sputtering surface analysis such as secondary ion mass spectrometry (SIMS), x-ray photoelectron spectroscopy (XPS), and Auger electron spectroscopy (AES) on a sample to be evaluated including a sheet metal and a semiconductor material.

2. Description of the Related Art

As a method of measuring the depth concentration profile of impurities within semiconductor material such as a sheet metal and a complementary metal oxide semiconductor (CMOS), there have been. known SIMS, XPS, and AES, which are depth analysis methods for the composition of a thin film surface. These methods of depth analysis irradiate the surface of a sample with ion beams from some 100 eV to some 10 keV and sputter atoms from the sample surface, hence to do depth analysis of the elements present in the vicinity of the sample surface.

These depth analysis methods of the composition on the sample surface, however, have such a problem that they cannot correctly estimate depth profile of a very thin film and a sharp dept profile of impurities because the atoms on the sample surface are mixed together in some deep region through irradiation of the energized ion beams (mixing effect). Here, the lower energy of irradiating ion beams may be used, but in the case of measuring an extremely thin film (for example, a thin film of 5 nm or less) or a sharp impurity profile (for example, depth profile of the impurity elements ion-implanted with an energy of 1 keV or less), it is impossible even by use of ion beams of the lower energy (1 keV or less), to obtain the true depth concentration profile owing to the mixing effect caused by the primary ions within the sample. Although the energy of the ion beam may be further lowered, a lower limit for the energy may be set to 200 eV, taking the performance of an ion gun into consideration in the present circumstances. Even when an ion gun which can emit ion beams of 100 eV or less is developed in the future, there occurs little ion sputtering in ion beams of 100 eV or less, hence to make it impossible to do analysis.

Owing to this restriction on the analysis, in order to obtain a true, or an approximately true depth profile, there arises a necessity of using a deconvolution analysis method for estimating the true depth profile from the measured depth profile, considering the depth resolution concerned with the phenomenon caused by the ion sputtering, such as the mixing effect. Specifically, assuming that a measured profile is defined as $I(z)$, a depth resolution function, a function representing the distortion caused by analysis, is defined as $g(z)$, and that a true depth profile is defined as $X(z)$, these three functions can be expressed in equation (1) (See FIG. 12):

$$I(z) = \int X(z')g(z-z')dz' \quad (1)$$

In short, the deconvolution analysis method is a method for estimating a true depth profile $X(z)$ from $I(z)$ considering this depth resolution function $g(z)$.

In the phenomenon occurring in the initial sputtering in the vicinity of the sample surface, when the sample surface is irradiated with any other elements than rare gas, since the atomic species irradiated as ion remains on the sample surface, its concentration gradually increases until it becomes constant (it reaches the steady state). In other words, in the initial sputtering, the concentration of the atomic species of the ion irradiated on the sample surface and the atomic species forming the sample surface varies gradually. Even when rare gas is used as the irradiating ionic species, when the atomic species forming the sample surface is two types and more (for example, $SiO_2$, NiSi, GaAs, and so on), a phenomenon called selective sputtering occurs, although it depends on the irradiation conditions such as energy and incident angle, and the concentration of the atomic species of the irradiated ion on the sample surface and the atomic species forming the sample surface will gradually change until it reaches the steady state.

When the concentration of the atomic species forming the sample surface changes, the depth of sputtering per time unit, namely the sputtering rate also changes simultaneously. That is, the measured depth profile becomes different from the actual depth profile, owing to a change in the sputtering rate. Therefore, in the case of deconvolution analysis on the depth profile of concentrated boron present in the vicinity of the surface, the depth profile distorted by a change of the sputtering rate has to be returned to the accurate profile and analyzed; otherwise, a wrong profile would be obtained.

According to C. F. McConville, S. H. Al-Harthi, M. G. Dowsett, F. S. Gard, T. J. Ormsby, B. Guzman, T. C. Q. Noakes, P. Bailey, J. Vac. Sci. Technol. B20 (2002) 1690 (hereinafter, "C. F. McConville et al."), in the case of sputtering a Si sample with oxygen ion beams, medium energy ion scattering (MEIS) measures that in the initial sputtering, the sputtering rate changes in the dept direction (the sputtering rate is greatest on the uppermost surface and then gradually decreases, to a constant value). More specifically, a sample whose surface was amorphized with about 15 nm is irradiated with ion and at once measured in the MEIS, thereby obtaining the decreasing amount in the width of the amorphous region, in the other words, the relationship between the sputtered depth and the ion irradiation dose.

L. Shao, J. Liu, C. Wang, K. B. Ma, J. Zhang, J. Chen, D. Tang, S. Patel, W. K. Chu, Appl. Phys. Lett. 83(2003) 5467 (hereinafter, "L. Shao et al.") discloses a technique of converting an apparent depth profile distorted by a change of the sputtering rate into a true depth profile by calibrating the depth change of the sputtering rate in a depth direction in the initial sputtering. According to this technique, the apparent depth when it is calibrated assuming that the sputtering rate is constant in the depth direction, is corrected by using equation (2):

$$Z_{real} = Z_{app} + a \times (1 - \exp(-b \times Z_{app})) \quad (2)$$

where $Z_{real}$ indicates the axis of an actual depth (nm), $Z_{app}$ indicates the axis of an apparent depth (nm) calibrated. assuming that the sputtering rate is constant in the depth direction, and a and b indicates coefficients (nm, $nm^{-1}$).

In the case of using SIMS, since the signal intensity (secondary ion intensity Y) obtained depending on a change in the sputtering rate also changes, it is necessary to calibrate the signal intensity in equation (3):

$$Y_{real} = Y_{app}/(1 + a \times b \times \exp(-b \times Z_{app})) \quad (3)$$

In AES and XPS, calibration by equation (3) is not necessary.

The parameters a and b of equation (2) may be derived from the result of MEIS measurement like C. F. McConville et al., or they may be estimated from a comparison of the measurement profile between an ion-implanted sample and a capped sample with a film some nm to some 10 nm thick of the same material as the substrate. In the latter method, the sputtering rate becomes constant in the ion-implanted region by depositing the film of the same material there, a comparison between this depth profile and the depth profile for the ion-implanted sample (sample without cap film) has only to be made, so to estimate the parameters a and b.

However, after the concentrated boron profile (formed by the ion implantation) present in the vicinity of the surface is measured by the SIMS, when the obtained data is calibrated with the sputtering rate in the method of L. Shao et al. and analyzed with deconvolution, a depth profile indicating a physically impossible structure (a concentration of zero in the vicinity of the surface and the vibration structure in the vicinity of the depth 2 to 3 nm) is derived in the initial sputtering disadvantageously. L. Shao et. al. discloses that this peak of about 10 at % concentration is significantly larger. This peak would be considered an artifact on the deconvolution analysis. This is because of the following reasons.

It can be easily understood that in the region where the concentration of the atomic species forming the sample surface gradually changes in the initial sputtering and the sputtering rate also changes, the depth resolution function also changes in parallel. When such an analysis condition is used that sputtering causes no surface roughness, the depth resolution function is considered to be constant at a certa depth and more. Although a test of examining a change in the depth resolution from the uppermost surface to a point when it becomes constant has not been reported, the change is assumed as follows. In the right initial sputtering (when one ion beam first bumps against the sample), naturally no mixing occurs in the sample and so the depth resolution function is a delta function. When the sputtering comes into a constant state and the sputtering rate becomes constant, since the depth resolution function is in a shape of having some width, it is naturally considered that the depth resolution function is changing between a period from the right initial sputtering to the time when the sputtering rate becomes constant.

Namely, when the depth profile of the concentrated boron present in the vicinity of the surface is analyzed with deconvolution, since the concentrated boron is distributed in the region where the depth resolution varies, a change in the depth resolution has to be taken into consideration together with a change in the sputtering rate. Otherwise, a wrong depth profile would be derived.

SUMMARY OF THE INVENTION

According to one aspect of the present invention, a deconvolution analysis apparatus includes a sputtering rate calibrating unit that calibrates a depth profile resulting from a depth analysis on a sample to be estimated by using a sputtering surface analysis, according to a depth change of a sputtering rate in an initial sputtering; and a deconvolution analysis unit that performs a deconvolution analysis on the depth profile whose depth axis is extended, so as to make a depth change of a depth resolution in the initial sputtering apparently constant.

According to another aspect of the present invention, a deconvolution analysis apparatus includes a depth profile obtaining unit that obtains a depth profile resulting from a depth analysis on a sample to be estimated by using a sputtering surface analysis; function parameters estimating unit that estimates parameters of a depth resolution function indicating an analytical distortion in the depth sputtering analysis on the sample; a sputtering rate calibrating unit that calibrates the depth profile according to the depth change of the sputtering rate in the initial sputtering; a depth axis calibrating unit that extends the depth axis of the calibrated depth profile so as to make the depth resolution change in the initial sputtering apparently constant; an interpolating unit that forms $2^n$ data points in the depth profile with the depth axis extended and spaces the data points equally, where n is a natural number; a depth resolution function creating unit that creates profile data of depth resolution functions by using the depth resolution function parameters, according to a number of data points and intervals between the data points in the interpolated depth profile; an analysis unit that performs a deconvolution analysis according to the created depth resolution function profile data and the depth profile; and a depth axis inversely calibrating unit that returns the depth axis with the data extended, analyzed with deconvolution, to the actual depth axis.

According to still another aspect of the present invention, a computer program product having a computer readable medium including programmed instructions for deconvolution analysis, when executed by a computer, causes a computer to perform calibrating a depth profile resulting from a depth analysis on a sample to be estimated by using a sputtering surface analysis, according to a depth change of a sputtering rate in an initial sputtering; and performing a deconvolution analysis on the depth profile whose depth axis is extended, so as to make a depth change of a depth resolution in the initial sputtering apparently constant.

According to still another aspect of the present invention, a computer program product having a computer readable medium including programmed instructions for deconvolution analysis, when executed by a computer, causes a computer to perform obtaining a depth profile resulting from a depth analysis on a sample to be estimated by using a sputtering surface analysis; estimating parameters of a depth resolution function indicating an analytical distortion in the depth sputtering analysis on the sample; calibrating the depth profile according to the depth change of the sputtering rate in the initial sputtering; extending the depth axis of the calibrated depth profile so as to make the depth resolution change in the initial sputtering apparently constant; forming $2^n$ data points in the depth profile with the depth axis extended and spacing the data points equally, where n is a natural number; creating profile data of depth resolution functions by using the depth resolution function parameters, according to a number of data points and intervals between the data points in the interpolated depth profile; performing a deconvolution analysis according to the. created depth resolution function profile data and the depth profile; and returning the depth axis with the data extended, analyzed with deconvolution, to the actual depth axis.

According to still another aspect of the present invention, a deconvolution analysis method includes calibrating a depth profile resulting from a depth analysis on a sample to be estimated by using a sputtering surface analysis, according to a depth change of a sputtering rate in an initial sputtering; and performing a deconvolution analysis on the depth profile whose depth axis is extended, so as to make a depth change of a depth resolution in the initial sputtering apparently constant.

According to still another aspect of the present invention, a deconvolution analysis method includes obtaining a depth profile resulting from a depth analysis on a sample to be estimated by using a sputtering surface analysis; estimating parameters of a depth resolution function indicating an analytical distortion in the depth sputtering analysis on the sample; calibrating the depth profile according to the depth change of the sputtering rate in the initial sputtering; extending the depth axis of the calibrated depth profile so as to make the depth resolution change in the initial sputtering apparently constant; forming $2^n$ data points in the depth profile with the depth axis extended and spacing the data points equally, where n is a natural number; creating profile data of depth resolution functions by using the depth resolution function parameters, according to a number of data points and intervals between the data points in the interpolated depth profile; performing a deconvolution analysis according to the created depth resolution function profile data and the depth profile; and returning the depth axis with the data extended, analyzed with deconvolution, to the actual depth axis.

DETAILED DESCRIPTION OF THE EMBODIMENTS

Exemplary embodiments of a deconvolution analysis apparatus, a deconvolution analysis program, and a deconvolution analysis method according to the invention will be described in details with reference to the accompanying drawings.

Figure 1:
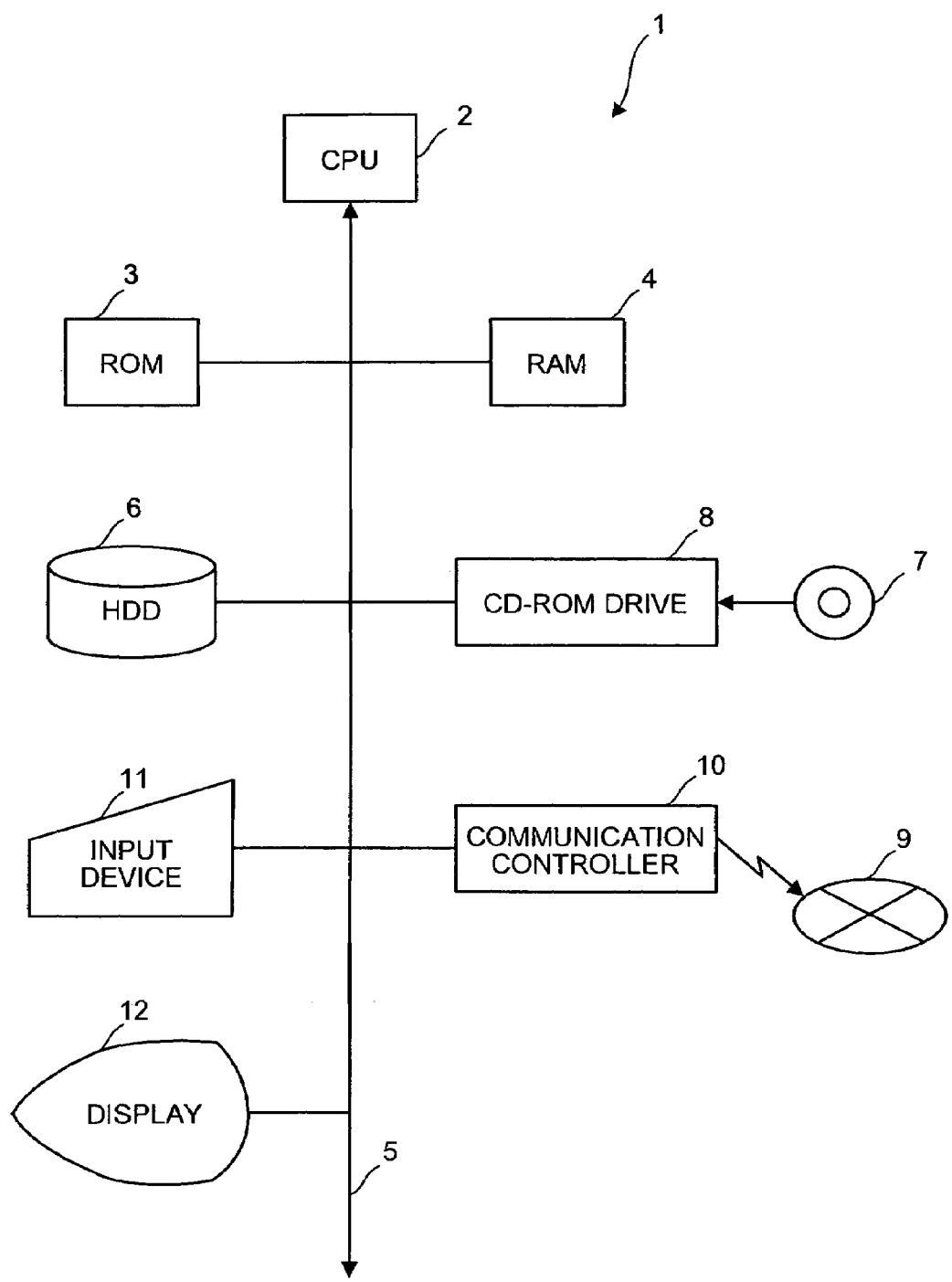
FIG. 1 is a block diagram showing the hardware structure of a deconvolution analysis apparatus according to one embodiment of the invention.

One embodiment of the invention will be described according to FIG. 1 to FIG. 11. FIG. 1 is a block diagram showing the hardware structure of a deconvolution analysis apparatus 1 according to the embodiment of the invention. As illustrated in FIG. 1, the deconvolution analysis apparatus 1 is, for example, a personal computer or a workstation, which includes a CPU (central processing unit) 2 that is the main portion of the computer for intensively controlling each unit. A ROM (read only memory) 3 of storing BIOS and a RAM (Random Access Memory) 4 capable of storing various data in a rewritable way is connected to this CPU 2 through a bus 5.

The bus 5 further connects an HDD (hard disk drive) 6 which stores various programs, a CD-ROM drive 8 which reads a CD-ROM (compact disc read only memory) 7 as a mechanism for reading computer software, a delivered program, a communication controller 10 which controls communication between the deconvolution analysis apparatus 1 and a network 9, an input device 11 for making various instructions at an analysis time such as a keyboard and a mouse, and a display 12 for displaying the analytical results, such as a CRT (cathode ray tube) or an LCD (liquid crystal display), through I/O not illustrated.

The RAM 4 works as a buffer serving as a working area of the CPU 2 because of having the ability to store various data in a rewritable way.

The CD-ROM 7 shown in FIG. 1 works as the storing medium of this invention, which stores OS (operating system) and various programs. The CPU 2 reads the program stored in the CD-ROM 7 through the CD-ROM drive 8 and installs it into the HDD 6.

As the storing medium, not only the CD-ROM 7 but also various kinds of media can be used including an optical disk such as a DVD (digital versatile disk), an optical magnetic disk, a magnetic disk such as flexible disk, and a semiconductor memory. A program may be downloaded from the network 9 such as the Internet through the communication controller 10 and installed into the HDD 6. In this case, a storing device which stores the program in the server on the transmission side is also the storing medium of this invention. A program may be operated on a predetermined OS and in this case, it may make the OS take over one of various processing described later, or it may be included in one program file forming predetermined application software or OS.

The CPU 2 which controls the whole system performs various processing according to a program loaded into the HDD 6 used as the main memory of this system.

A characteristic function of the deconvolution analysis apparatus 1 according to the embodiment will be described this time, of the functions performed by the CPU 2 according to the various programs installed into the HDD 6 of the deconvolution analysis apparatus 1. The deconvolution analysis function performed by the CPU 2 according to the deconvolution analysis program will be described here. The deconvolution analysis function is to perform a deconvolution analysis on a depth concentration profile measured by SIMS, XPS, and AES.

Here, the depth analysis method of the composition of a thin film on the surface, including SIMS, XPS, and AES will be briefly described.

SIMS is to perform the depth profiling of the elements on a sample surface by irradiating the sample surface with ion beams called primary ions from some 100 eV to some 10 keV and detecting and measuring the secondary ions emitted through sputtering on the sample surface according to the mass spectrometric analysis. The ionic species may be single element or molecular or cluster including one of oxygen, fluorine, chlorine, carbon, cesium, rubidium, potassium, gallium, gold, bismuth, germanium, indium, neon, argon, krypton, xenon, osmium, iridium, rhodium, and ruthenium.

AES and XPS are to perform the depth profiling of the elements on a sample surface by irradiating the sputtered surface with electrons or X-ray to generate Auger electrons or photoelectrons and analyzing and detecting their electronic energy.

Figure 2:
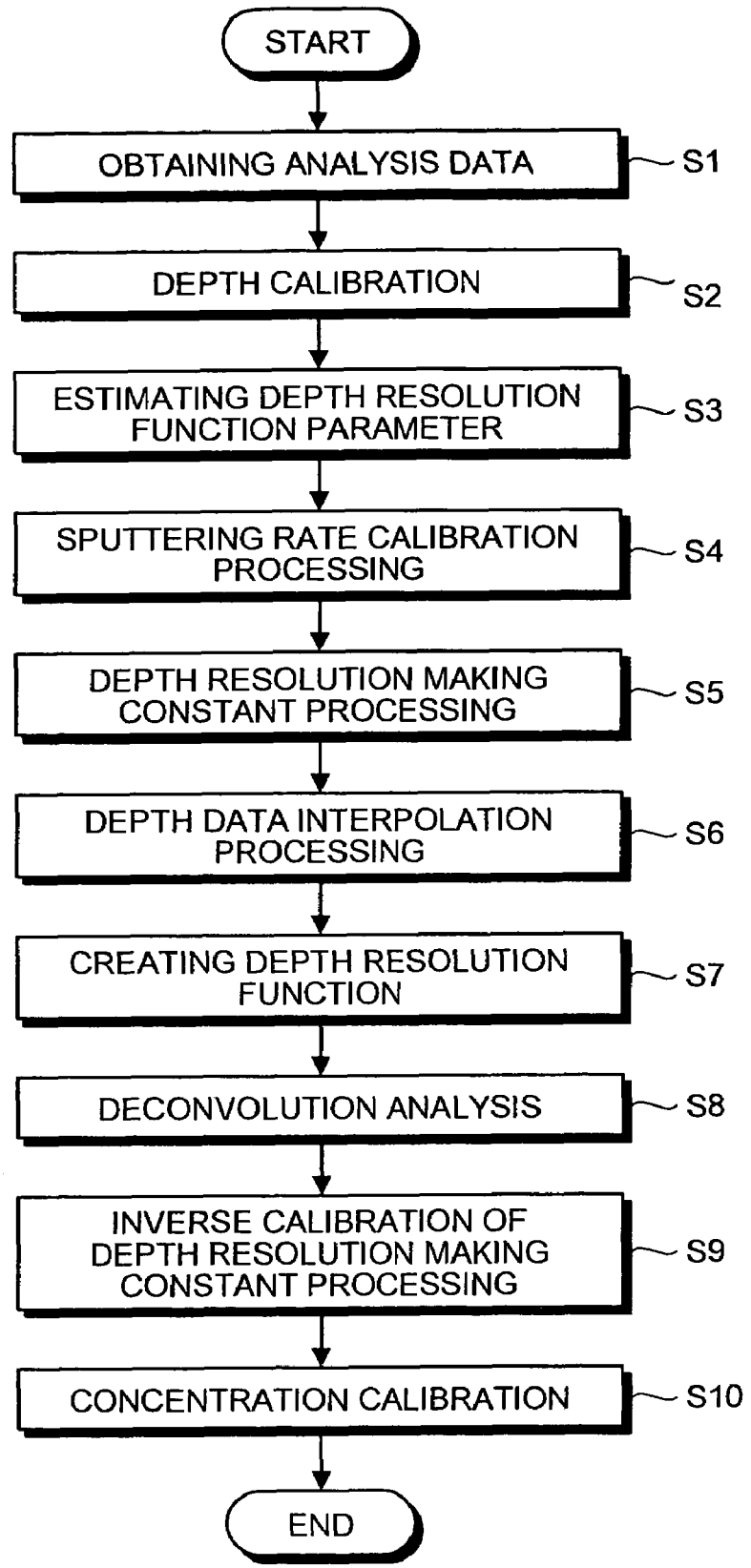
FIG. 2 is a flow chart showing the flow of the deconvolution analysis processing.

This time, the deconvolution analysis processing to be performed by the CPU 2 of the deconvolution analysis apparatus 1 will be described. FIG. 2 is a flow chart showing the flow of the deconvolution analysis processing. As illustrated in FIG. 2, analysis data is obtained through depth profiling of the elements on a sample surface according to one of SIMS, XPS, and AES (step S1). A horizontal axis of the obtained data indicates sputtering time and a vertical axis indicates signal intensity. Here, a function of depth profile obtaining means is performed.

In the following step S2, the horizontal axis (sputtering time) of the depth profile obtained in step S1 is changed into depth.

In order to do the depth calibration, the crater depth obtained through the sputtering may be measured with a stylus profilometer or a multi delta-layered sample whose intervals of depth between each delta layer are well known may be used. When the depth of a crater is 50 nm or less, a stylus profilometer cannot measure it accurately, so the latter method would be preferable. When the latter method is used, the composition of the multi delta-layered sample has to be equal to that of a sample to be measured and they should be sputtered under completely the same sputtering conditions. In order to calibrate the depth by using the crater depth obtained with the stylus profilometer, an average sputtering rate (depth/time) is calculated from the time and depth required for the sputtering, the value is multiplied by every sputtering time at each data point, and then the depths at each data point can be obtained. In order to calibrate the depths by using the data of the multi delta-layered sample, a sputtering rate is calculated from the sputtering time and the known intervals of depth between the delta layers in the analysis data of the multi delta-layered sample, the value is multiplied by every sputtering time at each data point, and then the depth at each data point can be obtained.

In the following step S3, parameters of a depth resolution function are estimated. Here, function parameters estimating means is performed. In order to estimate parameters of a depth resolution function, the measurement data of the delta dope sample in which the profile obtained by the measurement becomes a depth resolution function as it is, has to be fitted with the depth resolution function (for example, the depth resolution function proposed disclosed in M. G. Dowsett, R. D. Barlow, P. N. Allen, J. Vac. Sci. Technol., B12(1994), 186). When a specified sample (for example, boron within silicon) is analyzed under a specified measurement condition (for example, sputtering with 500 eV oxygen ions (incident angle 0°) in the Secondary Ion Mass Spectrometry), since the depth resolution parameters at that time are known in, for example, D. P. Chu, M. G. Dowsett, Phys. Rev., B56 (1997), 15167, they may be used.

In the following step S4, the sputtering rate calibration processing for calibrating a depth change of the sputtering rate in the initial sputtering is performed. By doing this, the apparent depth profile distorted by a change in the sputtering rate can be converted into the true depth profile. Here, a function of sputtering rate calibrating means is performed.

The sputtering rate calibration processing can be performed in the method described in L. Shao et al. having been described in the background art. According to L. Shao et al., the relationship between the actual depth and the apparent depth when the sputtering rate is regarded as constant is calibrated by using equation (2). The calibration expression of the change in the sputtering rate is not restricted to equation (2).

In the case of using SIMS, since the signal intensity (secondary ion intensity Y) obtained depending on a change in the sputtering rate also changes, the signal intensity has to be calibrated by using equation (3). AES and XPS need no calibration by equation (3).

In order to estimate the parameters a and b of equation (2), they may be derived from the measurement result of the MEIS like C. F. McConville et al., or they may be estimated from a comparison of the measurement profile between an ion-implanted sample and a capped sample with a film some nm to some 10 nm thick of the same material as the substrate attached on the same sample. In the latter method, the sputtering rate becomes constant in the ion-implanted region by depositing the film of the same material, and therefore a comparison between this depth profile and the depth profile for the ion-implanted sample (sample without cap film) has only to be made, so to estimate the parameters a and b.

In the following step S5, the processing of making the depth resolution constant is performed to extend the depth axis of the depth profile. This is in order to make a depth change of the depth resolution in the initial sputtering apparently constant. Later, the above processing of making the depth resolution constant will be described in detail.

In the right initial sputtering (when one ion beam first bumps against a sample), naturally no mixing occurs in the sample and so the depth resolution function is a delta function. When the sputtering comes into a steady state and the sputtering rate becomes constant, since the depth resolution function is in a shape of having some width, it is considered that the depth resolution function is changing from the initial sputtering to the time when the sputtering rate becomes constant. Actually, however, it is impossible to perform a deconvolution analysis while changing the depth resolution function according to the depth. Instead of changing the depth resolution function, the horizontal axis of the depth profile obtained by the sputtering rate calibration is to be extended according to a change in the depth resolution function. Namely, this is to extend the horizontal axis of the data so as to make the depth resolution function apparently constant. Here, a function of depth axis calibrating unit is performed. Assume that the differential value $\Delta z$ of the horizontal axis of the depth profile data changes similarly to the sputtering rate according to equation (4):

$$\Delta Z_{reg} = \Delta Z_{real}/(1-\exp(-b \times Z_{app})) \quad (4)$$

In the case of using SIMS, since the integrated value of the signal intensity has to be identical when the horizontal axis changes, the signal intensity of the vertical axis has to be changed as equation (5):

$$Y_{reg}=Y_{real}\times(1-\exp(-b\times Z_{app})) \quad (5)$$

where $\Delta Z_{reg}$ and $Y_{reg}$ respectively indicate the differential value of the horizontal axis and the signal intensity of the vertical axis in the depth resolution function making constant data. The parameter b in equations (4) and (5) may be derived from the measurement result of MEIS like C. F. McConville et al., or it may be estimated from a comparison of the measurement profile between the ion-implanted sample and the capped sample with a film some nm to 10 nm thick of the same material as the substrate. An equation for extending the depth axis of the depth profile in order to make a depth change of the depth resolution apparently constant is not restricted to equation (4).

Thus, a depth change in the depth sputtering rate in the initial sputtering is calibrated by using equations (2) and (4) (also using equations (3) and (5) in the case of using SIMS), and further the depth axis in the depth profile can be extended so as to make a dept change of the depth resolution in the initial sputtering apparently constant. Needless to say, the calibration method of the sputtering rate change and the extending method of the depth axis in the depth profile may be changed according to the type of a material to be measured, the type of ion for use in the measurement, and the irradiation conditions (energy and incident angle).

In the following step S6, data interpolation processing is performed. In the depth profile in which the depth resolution making constant processing has been performed in step S5, the intervals of depth between each data point forming this depth profile are not constant. Since the deconvolution analysis processing described later is generally calculated by using the Fourier space, every data point forming the depth profile has to be spaced equally and the number of the data points has to be $2^n$ (n=2, 3, 4, 5, 6, 7, 8, 9, 10, . . .). Therefore, it is necessary to do the interpolation processing of the depth profile data including the number $2^n$ of the data points (a process in which the distance between $2^n$ data points are spaced equally). A function of interpolation means is performed here.

In the following step S7, the profile data of the depth resolution function is created by using the depth resolution function parameters obtained in step S3. The intervals between each data point and the number of data have to be the same as those of the depth profile having been created in step S6. A function of depth resolution function creating means is performed here.

In the following step S8, the deconvolution analysis result is obtained from the depth resolution function profile data obtained in Step S7 and the depth profile obtained in step S6 by using the deconvolution analysis including the maximum entropy method (MEM method) and the Fourier transform. A function of analyzing means is performed here. At this time, it is necessary to do the deconvolution analysis with the original point of the depth resolution function positioned as the centroid of this function.

In the following step S9, the inverse calibration of the depth resolution making constant processing is performed. Since the horizontal axis of the data obtained by the deconvolution analysis is in an extended state because of making the depth resolution function apparently constant, it has to be returned to the actual depth axis. More specifically, $\Delta Z_{reg}$ can be changed into $\Delta Z_{real}$ according to the relation as equation (6):

$$\Delta Z_{real}=\Delta Z_{reg}\times(1-\exp(-b\times Z_{app})) \quad (6)$$

In the case of using SIMS, since the vertical axis has to be changed, $Y_{reg}$ can be changed into $Y_{real}$ according to the relation of equation (7):

$$Y_{real}=Y_{reg}/(1-\exp(-b\times Z_{app})) \quad (7)$$

This results in getting a true depth profile. A function of depth axis inverse calibration means is performed here.

At last, in step S10, a relative sensitivity factor, a concentration conversion factor, is obtained from the standard sample whose concentration is known, and the true depth profile obtained in step 9 is converted into the true depth profile by using the coefficient. Namely, the true concentration depth profile can be obtained by converting the vertical axis of the ion intensity into concentration. This concentration conversion is to be performed according to necessity and it does not necessarily have to.

Figure 3:
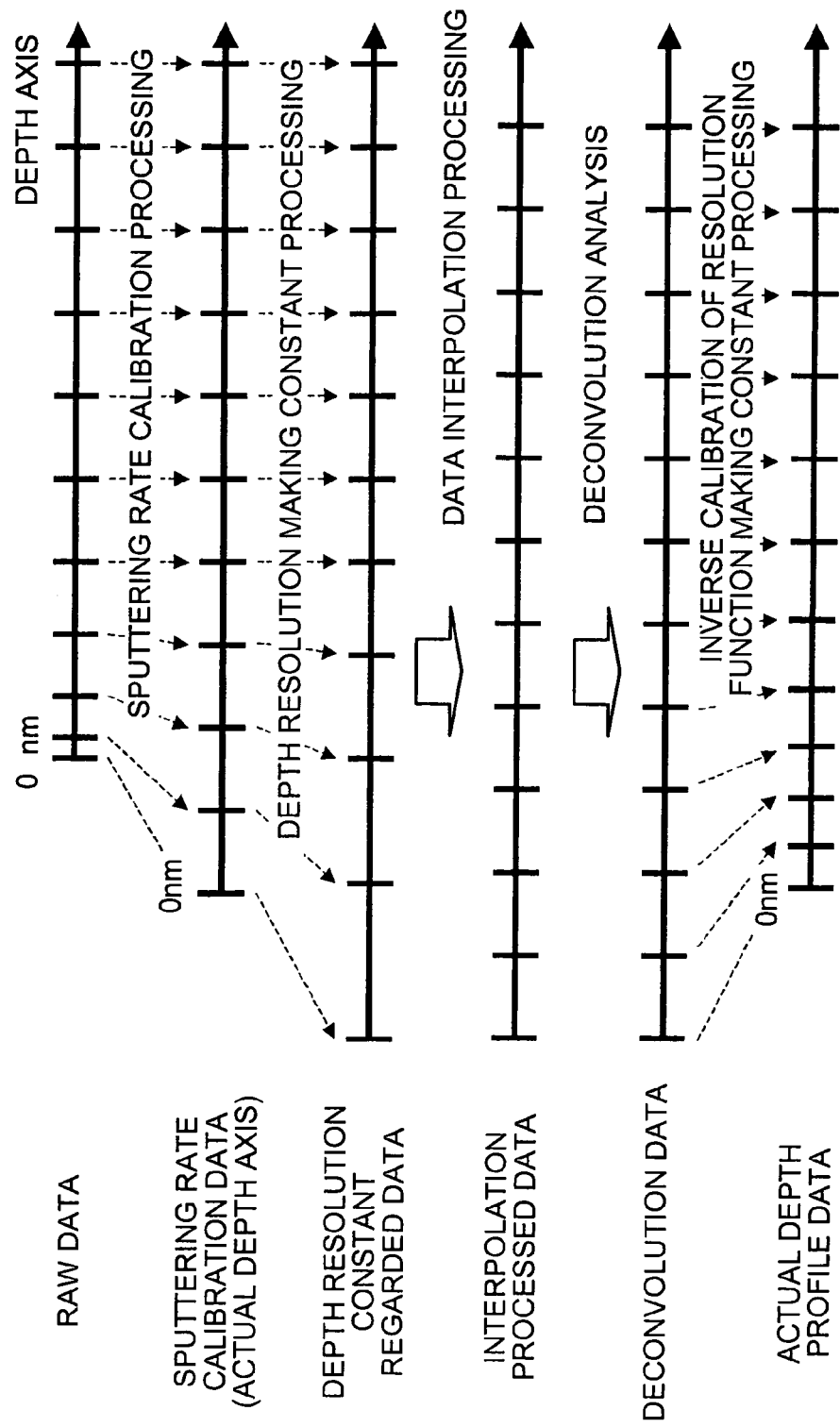
FIG. 3 is a view for use in describing a change in the horizontal axis (depth axis) of the depth profile data in the deconvolution analysis processing.

FIG. 3 shows a change in the horizontal axis (depth axis) of the depth profile data in a series of the above-mentioned deconvolution analysis processing.

According to the embodiment, the depth profile resulting from the depth analysis on a sample to be estimated according to the sputtering surface analysis is calibrated according to a depth change of the depth sputtering rate in the initial sputtering, and the depth axis in the depth profile in which the depth resolution change in the initial sputtering has been calibrated so as to be apparently constant is extended, hence to do the deconvolution analysis. More specifically, the depth profile resulting from the depth analysis on the sample obtained to be estimated according to the sputtering surface analysis is calibrated according to a depth change of the depth sputtering rate in the initial sputtering, the depth axis of the calibrated depth profile is extended, the depth profile with the depth axis extended is formed by the number $2^n$ of the data points, data points are interpolated in an equally spaced way, the profile data of the depth resolution function is created by using the depth resolution function parameters according to the intervals between each data point and the number of data in the interpolated depth profile, the deconvolution analysis is performed according to the created depth resolution function profile data and the interpolated depth profile, and the depth axis with the data extended, analyzed with deconvolution, is returned to the actual depth axis. Thus, it is possible to analyze an extremely thin film present on the uppermost surface of a sample (for example, a thin film of 5 nm or less) or an extremely sharp impurity profile (for example, depth profile of the impurity elements ion-implanted at an energy of 1 keV or less) in a correct depth profile, and it is also possible to estimate a sample such as a sheet metal and a semiconductor material accurately, thereby increasing the efficiency in the research and development. For example, the impurities ion-implanted on a silicon sample called a shallow junction (for example, boron, arsenic, phosphorus, and so on) are present intensively in the vicinity of the sample surface and therefore, the use of the invention helps to obtain an accurate ion implantation profile.

As example 1, a sample is prepared, in which $^{11}B$ (boron of mass number 11) is ion-implanted on a Si (silicon) semiconductor under the condition of an energy 0.2 keV and the dose of $1\times10^{15}$ $cm^{-2}$. When this ion-implanted sample is measured by the secondary ion mass spectrometer under the condition of primary ion of $O_2^+$ 350 eV and incident angle 0°, a depth profile of boron (the vertical axis indicates the secondary ion intensity and the horizontal axis indicates the sputtering time) is obtained. This analysis data is entered into the deconvolution analysis apparatus 1 and processed according to the deconvolution analysis program (step S1 in FIG. 2).

Figure 4:
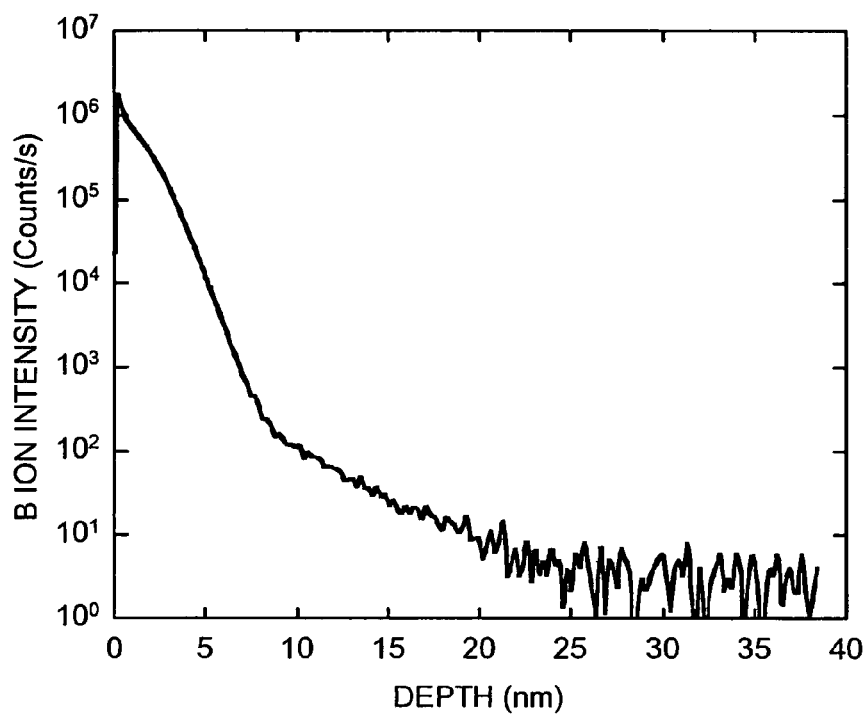
FIG. 4 is a graph showing the depth profile in which the horizontal axis of the measurement result of a sample with $^{11}$B (boron of mass number 11) ion-implanted is changed from the sputtering time to the depth.

A multi-delta sample with the intervals of depth 5 nm (a sample with boron delta-doped silicon in a multi layered way) is measured under the same measurement conditions and the horizontal axis of the measurement result of the above ion-implanted ample is changed from the sputtering time to the depth by using the sputtering rate (0.020 nm/sec) obtained from the measurement result of the sample. This result is shown in FIG. 4. Next, a sample with boron delta-doped on a silicon in a single layered way is measured under the same condition as mentioned above and the depth is calibrated by using the above-mentioned sputtering rate (step S2 in FIG. 2). This result is shown in FIG. 5.

Figure 5:
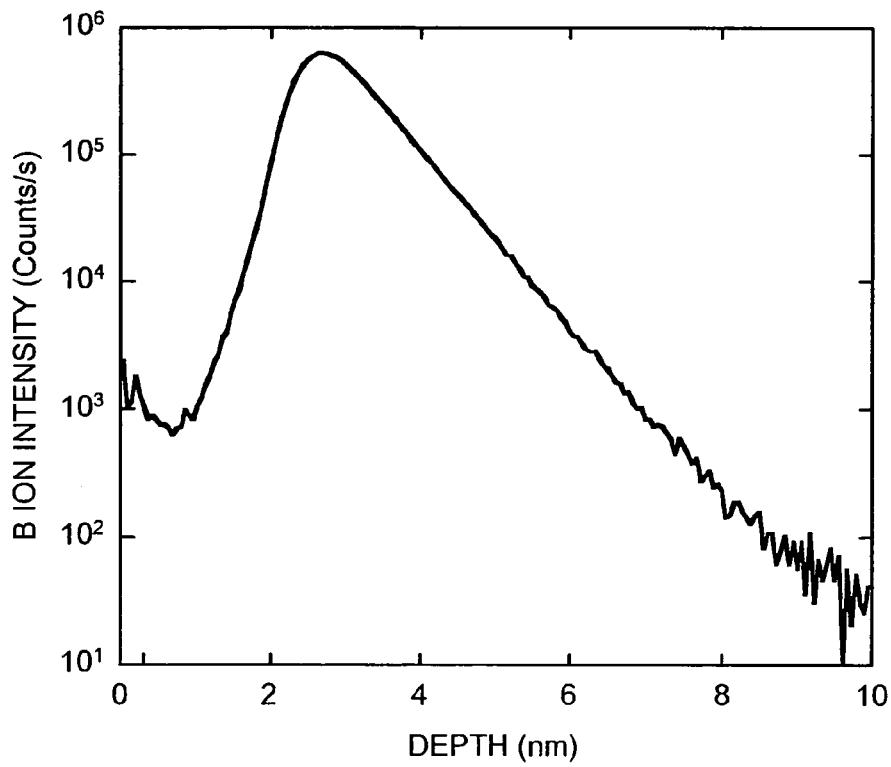
FIG. 5 is a graph showing the depth profile in which the horizontal axis of the measurement result of a sample with boron delta-doped in a single layer is changed from the sputtering time to the depth.

The depth profile shown in FIG. 5 is fitted according to the depth resolution function proposed in M. G. Dowsett, R. D. Barlow, P. N. Allen, J. Vac. Sci. Technol., B12 (1994), 186.:

$$R(z)=A*(1+\mathrm{erf}\xi_1)\exp-[z/\lambda d - 0.5(\sigma/\lambda d)^2] \quad (8)$$

where $\xi_1=(z/\sigma-\sigma/\lambda d)/\sqrt{2}$, so that an decay length $\lambda d$ and a gauss width $\sigma$ ($\lambda_d$: 0.62 nm, $\sigma$: 0.29 nm), which are the depth resolution function parameters, are extracted (step S3 in FIG. 2). In the original equation, the term of increment $\lambda_g$ is included, but in D. P. Chu, M. G. Dowsett, Phys. Rev., B56 (1997), 15167, $\lambda g$ is 0 and so the expression of $\lambda_g$ is removed from equation (8).

Figure 6:
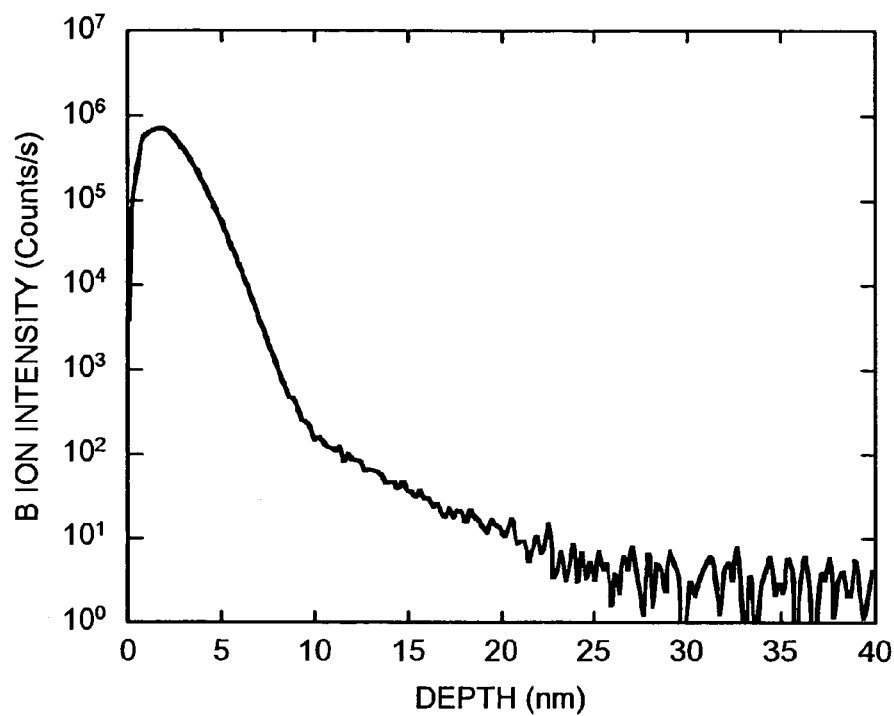
FIG. 6 is a graph showing the depth profile in which the sputtering rate has been calibrated as for the depth profile in FIG. 4.

The apparent depth distorted by the sputtering rate change is converted into the true depth by using equation (2) and the secondary ion intensity changing depending on the sputtering rate change is calibrated by using equation (3) (step S4 in FIG. 2). The depth profile obtained through this calibration is shown in FIG. 6.

In order to make the depth change of the depth resolution apparently constant, the depth axis in the depth profile is extended by using equation (4) and the secondary ion intensity changing according to the extension of the depth axis is calibrated by using equation (5) (step S5 in FIG. 2). The depth profile obtained through this calibration is shown in FIG. 7.

Figure 7:
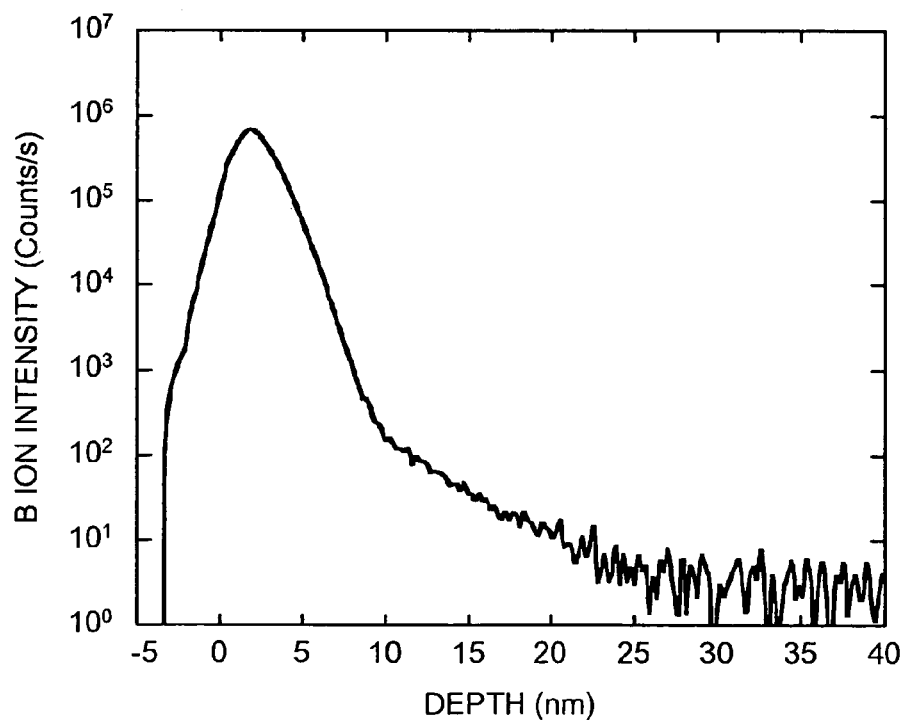
FIG. 7 is a graph showing the depth profile in which in order to make the depth resolution change apparently constant, the depth axis of the depth profile is extended and the secondary ion intensity changing according to the extension of the depth axis is calibrate.

The data interpolation processing is performed so as to make each interval between each data point equal and make the number of the points 512 in the depth profile data shown in FIG. 7 (step S6 in FIG. 2).

Figure 8:
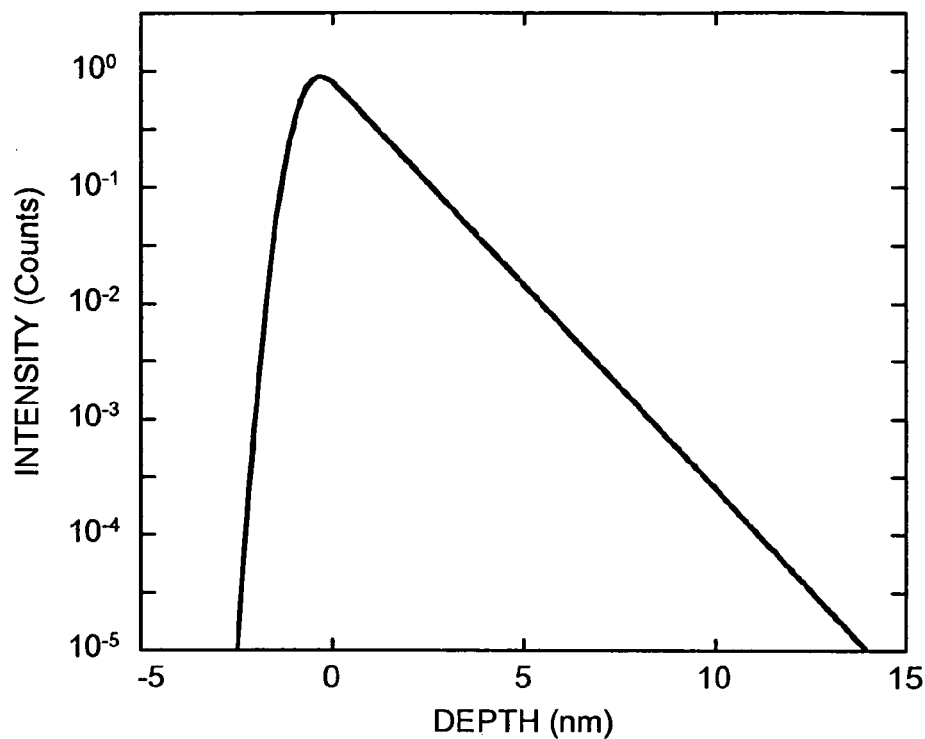
FIG. 8 is a graph showing the profile data of the depth resolution function.

The profile data of the depth resolution function is created (step S7 in FIG. 2) by using the depth resolution function parameters, the decay length $\lambda_d$ and the gauss width $\sigma$ ($\lambda_d$: 0.62 nm, $\sigma$: 0.29 nm) extracted in step S3. At this time, the interval between each data point and the number of data should be equal to the data point interval and the data number (512 points) of the above created depth profile. The profile data of the depth resolution function obtained through this processing is shown in FIG. 8.

The deconvolution analysis result is obtained from the depth resolution function data created in step S7 and the depth profile date interpolated in step S6 by using the deconvolution analysis method based on the maximum entropy method (MEM method) (step S8 in FIG. 2). At this time, the deconvolution analysis is performed with the original point of the depth resolution function positioned as the centroid of this function.

In order to return the horizontal axis of the data obtained through the deconvolution analysis to the actual depth axis, the depth axis of the horizontal axis is converted by using the relation of equation (6) and the signal intensity of the vertical axis is converted by using the relation of equation (7) (step S9 in FIG. 2). Thus, a true depth profile can be obtained.

At last, a relative sensitivity factor, a concentration conversion factor is obtained from the standard sample (boron doped sample with boron concentration $5.0\times10^{18}$ cm$^{-3}$), and this factor is used so as to convert the true depth profile obtained previously into the true concentration depth profile (step S10 in FIG. 2). The concentration depth profile obtained through this concentration calibration is shown in FIG. 9.

Figure 9:
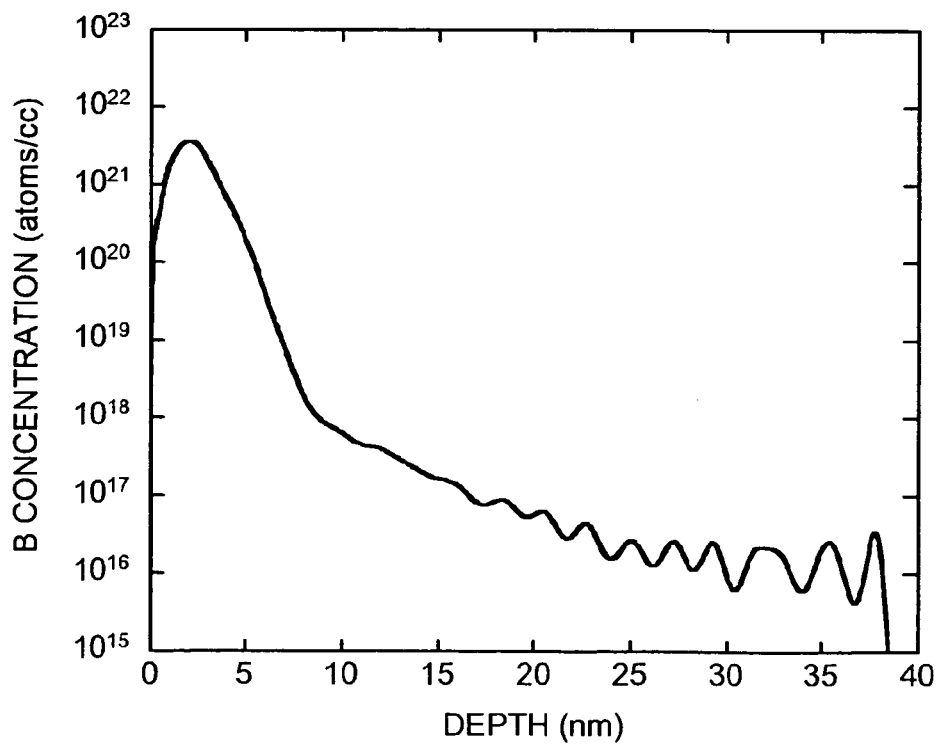
FIG. 9 is a graph showing the depth concentration profile obtained through the concentration calibration.

The profile shown in FIG. 9 shows the ideal ion implantation profile and it completely agrees with the result obtained in the back-side secondary ion mass spectrometry (it is a method of fully removing the back side of a substrate and analyzing from the backward, in which a fairly true profile can be obtained without being influenced by the mixing effect). Therefore, the obtained profile is considered to be a true or approximately true profile.

Figure 10:
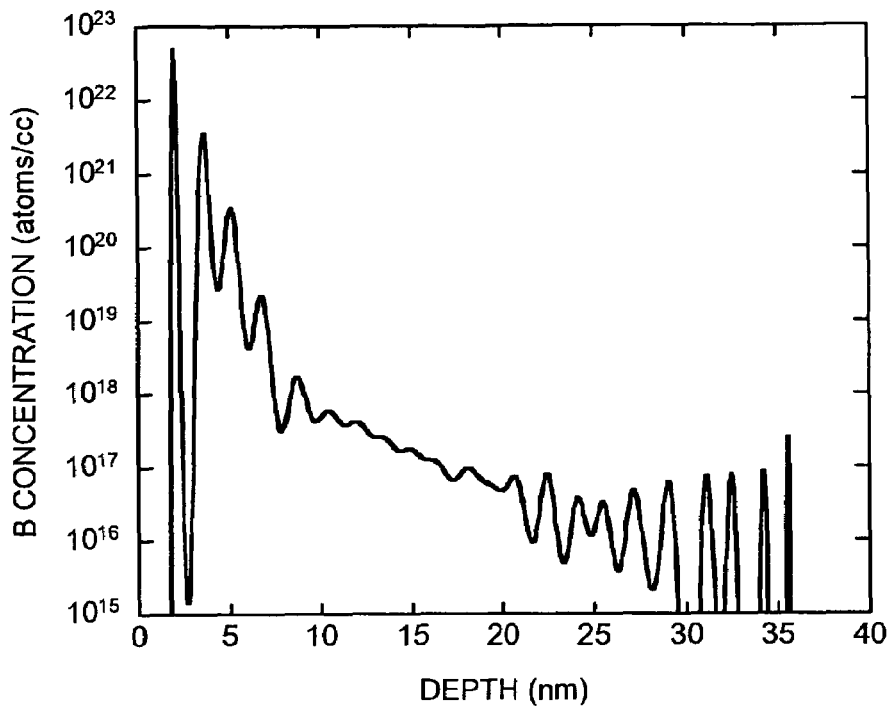
FIG. 10 is a graph showing the result of deconvolution of the depth profile, without the sputtering rate calibration processing and the depth resolution making constant processing.

As comparable example 1, the result of deconvolution of the depth profile obtained through the secondary ion mass analysis in example 1, without the sputtering rate calibration processing and the depth resolution making constant processing, is shown in FIG. 10. It shows the profile having the vibration structure which is physically impossible for the ion implantation profile and it proves that this deconvolution analysis result is not correct.

Figure 11:
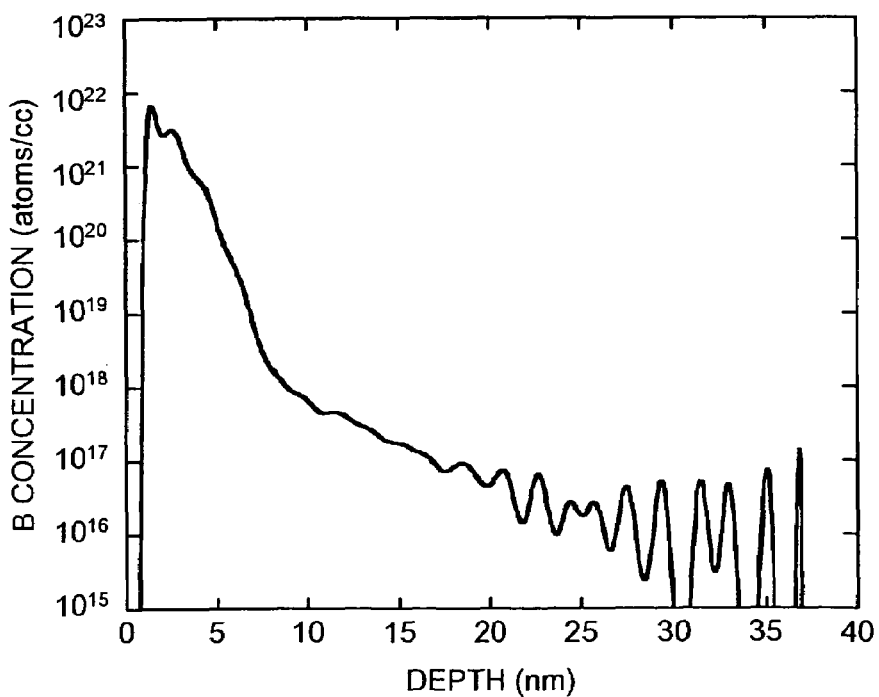
FIG. 11 is a graph showing the result of deconvolution of the depth profile, with the sputtering rate calibration processing, without the depth resolution making constant processing.
Figure 12:
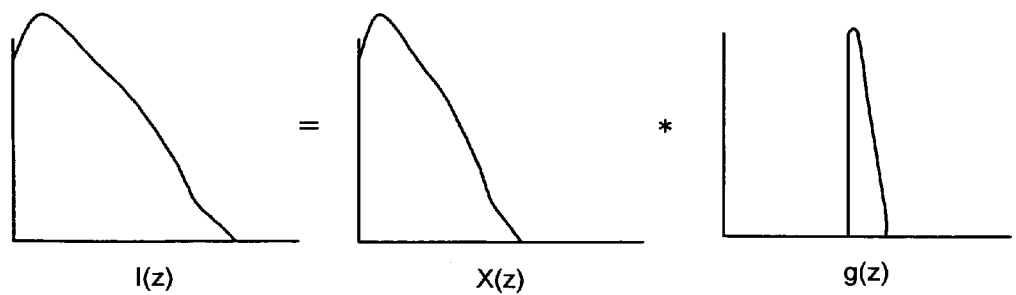
FIG. 12 is a view for use in describing the deconvolution analysis method of estimating a true depth profile from the measured depth profile.

As comparable example 2, the result of deconvolution of the depth profile obtained through the secondary ion mass analysis in example 1, only with the sputtering rate calibration processing, without the depth resolution making constant processing, is shown in FIG. 11. The tail portion of the depth profile is substantially identical to the result of example 1, but the concentration is zero in the vicinity of the surface and the depth profile shows an abnormal vibration structure in the region of 2 to 3 nm depth. It proves that this deconvolution analysis result is not correct.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A deconvolution analysis apparatus comprising:
   a sputtering rate calibrating unit that calibrates a depth profile resulting from a depth analysis on a sample to be estimated by using a sputtering surface analysis, according to a depth change of a sputtering rate in an initial sputtering; and
   a deconvolution analysis unit that performs a deconvolution analysis on the depth profile whose depth axis is extended, so as to make a depth change of a depth resolution in the initial sputtering apparently constant.

2. A deconvolution analysis apparatus comprising:
   a depth profile obtaining unit that obtains a depth profile resulting from a depth analysis on a sample to be estimated by using a sputtering surface analysis;

a function parameter estimating unit that estimates parameters of a depth resolution function indicating an analytical distortion in the depth sputtering analysis on the sample;

a sputtering rate calibrating unit that calibrates the depth profile according to the depth change of the sputtering rate in the initial sputtering;

a depth axis calibrating unit that extends the depth axis of the calibrated depth profile so as to make the depth resolution change in the initial sputtering apparently constant;

an interpolating unit that forms $2^n$ data points in the depth profile with the depth axis extended and spaces the data points equally, where n is a natural number;

a depth resolution function creating unit that creates profile data of depth resolution functions by using the depth resolution function parameters, according to a number of data points and intervals between the data points in the interpolated depth profile;

an analysis unit that performs a deconvolution analysis according to the created depth resolution function profile data and the depth profile; and a depth axis inversely calibrating unit that returns the depth axis with the data extended, analyzed with deconvolution, to the actual depth axis.

3. The deconvolution analysis apparatus according to claim 2, wherein
the depth axis calibrating unit changes signal intensity according to a change in the depth axis when secondary ion mass spectrometry is used as a surface analysis method.

4. The deconvolution analysis apparatus according to claim 2, wherein
the depth axis calibrating unit changes a differential value $\Delta Z_{reg}$ of the depth axis in the depth profile as $$\Delta Z_{reg} = \Delta Z_{real}/(1-\exp(-b \times Z_{app}))$$

where $\Delta Z_{reg}$ is a differential value of depth axis, $Z_{real}$ is an actual depth axis (nm), $Z_{app}$ is an apparent depth axis calibrated assuming that the sputtering rate is constant in a depth direction (nm), and b is a coefficient ($nm^{-1}$).

5. The deconvolution analysis apparatus according to claim 3, wherein
the depth axis calibrating unit changes the signal intensity $Y_{reg}$ as $$Y_{reg} = Y_{real} \times (1-\exp(-b \times Z_{app}))$$

where $Y_{reg}$ is a signal intensity, $Y_{real}$ is an actual signal intensity, $Z_{app}$ is an apparent depth axis calibrated assuming that the sputtering rate is constant in a depth direction (nm), and b is a coefficient ($nm^{-1}$).

6. A computer program product having a computer readable medium including programmed instructions for deconvolution analysis, wherein the instructions, when executed by a computer, cause the computer to perform:
calibrating a depth profile resulting from a depth analysis on a sample to be estimated by using a sputtering surface analysis, according to a depth change of a sputtering rate in an initial sputtering; and
performing a deconvolution analysis on the depth profile whose depth axis is extended, so as to make a depth change of a depth resolution in the initial sputtering apparently constant.

7. A computer program product having a computer readable medium including programmed instructions for deconvolution analysis, wherein the instructions, when executed by a computer, cause the computer to perform:

obtaining a depth profile resulting from a depth analysis on a sample to be estimated by using a sputtering surface analysis;

estimating parameters of a depth resolution function indicating an analytical distortion in the depth sputtering analysis on the sample;

calibrating the depth profile according to the depth change of the sputtering rate in the initial sputtering;

extending the depth axis of the calibrated depth profile so as to make the depth resolution change in the initial sputtering apparently constant;

forming $2^n$ data points in the depth profile with the depth axis extended and spacing the data points equally, where n is a natural number;

creating profile data of depth resolution functions by using the depth resolution function parameters, according to a number of data points and intervals between the data points in the interpolated depth profile;

performing a deconvolution analysis according to the created depth resolution function profile data and the depth profile; and returning the depth axis with the data extended, analyzed with deconvolution, to the actual depth axis.

8. The computer program product according to claim 7, wherein
the extending includes changing signal intensity according to a change in the depth axis when secondary ion mass spectrometry is used as a surface analysis method.

9. The computer program product according to claim 7, wherein
the extending includes changing a differential value $\Delta Z_{reg}$ of the depth axis in the depth profile as $$\Delta Z_{reg} = \Delta Z_{real}/(1-\exp(-b \times Z_{app}))$$

where $\Delta Z_{reg}$ is a differential value of depth axis, $Z_{real}$ is an actual depth axis (nm), $Z_{app}$ is an apparent depth axis calibrated assuming that the sputtering rate is constant in a depth direction (nm), and b is a coefficient ($nm^{-1}$).

10. The computer program product according to claim 7, wherein
the extending includes changing the signal intensity $Y_{reg}$ as $$Y_{reg} = Y_{real} \times (1-\exp(-b \times Z_{app}))$$

where $Y_{reg}$ is a signal intensity, $Y_{real}$ is an actual signal intensity, $Z_{app}$ is an apparent depth axis calibrated assuming that the sputtering rate is constant in a depth direction (nm), and b is a coefficient ($nm^{-1}$).

11. A deconvolution analysis method comprising:
calibrating a depth profile resulting from a depth analysis on a sample to be estimated by using a sputtering surface analysis, according to a depth change of a sputtering rate in an initial sputtering; and
performing a deconvolution analysis on the depth profile whose depth axis is extended, so as to make a depth change of a depth resolution in the initial sputtering apparently constant.

12. A deconvolution analysis method comprising:
obtaining a depth profile resulting from a depth analysis on a sample to be estimated by using a sputtering surface analysis;
estimating parameters of a depth resolution function indicating an analytical distortion in the depth sputtering analysis on the sample;

calibrating the depth profile according to the depth change of the sputtering rate in the initial sputtering;

extending the depth axis of the calibrated depth profile so as to make the depth resolution change in the initial sputtering apparently constant;

forming $2^n$ data points in the depth profile with the depth axis extended and spacing the data points equally, where n is a natural number;

creating profile data of depth resolution functions by using the depth resolution function parameters, according to a number of data points and intervals between the data points in the interpolated depth profile;

performing a deconvolution analysis according to the created depth resolution function profile data and the depth profile; and returning the depth axis with the data extended, analyzed with deconvolution, to the actual depth axis.

* * * * *